United States Patent
Beller et al.

(10) Patent No.: US 8,177,782 B2
(45) Date of Patent: May 15, 2012

(54) CONNECTION CABLE

(75) Inventors: Jürgen Beller, Gomaringen (DE); Martin Hagg, Wannweil (DE); Uwe Schnitzler, Tübingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 751 days.

(21) Appl. No.: 12/295,842

(22) PCT Filed: Mar. 20, 2007

(86) PCT No.: PCT/EP2007/002476
§ 371 (c)(1),
(2), (4) Date: Oct. 2, 2008

(87) PCT Pub. No.: WO2007/115655
PCT Pub. Date: Oct. 18, 2007

(65) Prior Publication Data
US 2010/0151722 A1    Jun. 17, 2010

(30) Foreign Application Priority Data

Apr. 5, 2006 (DE) .......................... 10 2006 015 972
May 15, 2006 (DE) .......................... 10 2006 022 606

(51) Int. Cl.
*A61B 18/04* (2006.01)
(52) U.S. Cl. ........................................................ 606/34
(58) Field of Classification Search ............... 606/34–40
See application file for complete search history.

(56) References Cited

U.S. PATENT DOCUMENTS

| 5,405,269 A | 4/1995 | Stupecky | |
|---|---|---|---|
| 6,685,701 B2* | 2/2004 | Orszulak et al. | 606/34 |
| 2004/0044339 A1* | 3/2004 | Beller et al. | 606/34 |

FOREIGN PATENT DOCUMENTS

| DE | 43 39 049 | 5/1995 |
| EP | 1180970 B1 | 8/2006 |
| JP | 2003-305050 A | 10/2003 |
| WO | WO 02/41798 | 5/2002 |

OTHER PUBLICATIONS

English Translation of Written Opinion of the International Searching Authority, Nov. 17, 2008 (5 pgs).

* cited by examiner

*Primary Examiner* — Christopher D Koharski
(74) *Attorney, Agent, or Firm* — Dickstein Shapiro LLP

(57) ABSTRACT

A connection cable which allows various high-frequency surgical instruments to be used with various high-frequency surgical devices. The connection cable includes a first connecting means designed for connection to a socket of the high-frequency surgical device and a second connecting means designed for connection to the high-frequency surgical instrument. A programmable memory is provided which is connected to contacts of the first connecting means and controls adjustment of the high-frequency surgical device. The adjustment of the high-frequency surgical instrument is controlled in accordance with stored data sets in order to adapt device settings to the particular high-frequency surgical instrument.

10 Claims, 1 Drawing Sheet

CONNECTION CABLE

FIELD OF THE INVENTION

The invention relates to a connection cable for connecting a high-frequency surgical instrument to a high-frequency surgical device, and in particular to a connection cable containing a programmable memory which allows a variety of high-frequency surgical instruments and high-frequency surgical devices to be interchangeably connected.

BACKGROUND OF THE INVENTION

There are several different types of high-frequency ("HF") surgical devices. HF surgical devices comprise, for example, at least one high-frequency generator for the generation of high-frequency electrical voltages or currents for the monopolar, bipolar or quasi bipolar cutting and/or coagulation of biological tissue. Appliances for the adjustment, monitoring, regulation, restriction and/or modulation of the HF voltages, HF currents, electrical arcs between an active electrode and biological tissue and/or the power required for the cutting and/or coagulation may also be provided. HF surgical devices can also be equipped with different operating modes for the cutting and/or coagulation processes, such as, for example, soft coagulation, forced coagulation, spray-coagulation, continuous cutting or fractionated cutting and automatic phase control. HF surgical devices can also be equipped with appliances for the manual and/or automatic activation and/or automatic deactivation, automatic limitation of the duration of activation, appliances for the automatic monitoring of different safety criteria, etc.

There are also several different types of HF surgical instruments. HF surgical instruments are also available as, for example, monofunctional, bifunctional or multifunctional instruments for monopolar, bipolar or quasi bipolar cutting and/or coagulation of biological tissue. Like HF surgical devices, HF surgical instruments are offered by different manufacturers in an extremely wide variety of forms.

The range of different instruments and devices available for high-frequency surgery has continuously increased in virtually all specialist surgical fields since the development of minimally invasive surgery. Connecting a particular high-frequency surgical instrument to a particular high-frequency surgical device requires appropriate adjustments to be made with respect to the output of the high-frequency surgical instrument. An incorrectly adjusted operating mode with respect to the connected HF surgical instrument or an HF voltage, HF power or HF power intensity which is adjusted too high can lead to destruction of an instrument which is unsuitable therefor or may harm the patient. The increase in the variety of instruments available has led to an increase in the requirements on the staff with respect to the correct adjustment of the HF surgical devices connected to the HF surgical instruments. In addition, a change of the HF surgical instrument used by the surgeon during an operation generally necessitates a change in the adjustment of the concomitantly used HF surgical device. This diverts the attention of the operation team away from the operation as they attend to the appropriate adjustments.

HF surgical instruments and devices include not only those which provide electrical power, but also those in which "mechanical" functions such as aspiration or rinsing are performed simultaneously.

In order to simplify the required adjustments on the connection of an HF surgical instrument to an HF surgical device, a proposal is known from DE 43 39 049 A1. A coding device is provided in the HF surgical instrument which programs the HF surgical device via connection plugs. For example, the coding device adjusts all the parameters of the HF surgical device in such a way that they match the HF surgical instrument. However, in this case, it is a precondition that the HF surgical instrument is adapted to the HF surgical device. In other words, the HF surgical instrument must be able to "understand" the HF surgical device. This kind of communication is not possible if operating HF surgical instruments using HF surgical devices from other manufacturers.

Therefore, it is desired to provide a solution which allows HF surgical instruments of different designs and/or from different manufacturers to be used with HF surgical devices of different designs and/or from different manufacturers.

SUMMARY

Disclosed embodiments include a connection cable including a first connecting means which is designed for connection to a socket of an HF surgical device and which is connected via a cable to a second connecting means, which is designed for connection to an HF surgical instrument. A programmable memory is also provided, which is connected to contacts of the first connecting means and is designed in such a way that a means for adjusting the HF surgical device (connected to the socket) can be controlled in accordance with a stored data set in order to adapt device settings to the particular HF surgical instrument.

According to disclosed embodiments, the coding devices are programmable and are installed in the connection cable rather than in the HF instrument. In other words, the connection cable containing the coding devices could be thought of as an "adapter cable." This makes it possible to convert "coding signals" present in the HF surgical instrument or output via its plug into "coding signals" which are compatible with a HF surgical device provided therefor, which are understood by the device.

In one embodiment, programming connections of the programmable memory are connected to contacts of the first or the second connecting means for programming the memory. Therefore, the memory does not require complicated externally tapped programming units. Instead, the connection cable can be programmed via these programming connections by the contacts of the connecting means.

BRIEF DESCRIPTION OF THE DRAWINGS

In the following, the invention will now be described in more detail with reference to an exemplary embodiment, which will be explained in more detail with reference to the enclosed drawings.

DETAILED DESCRIPTION OF THE INVENTION

Figure 1:
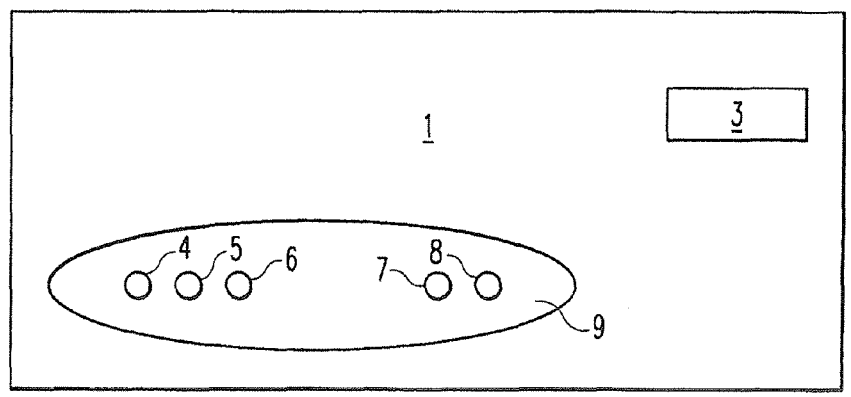
FIG. 1 is a schematic representation of an HF surgical device, used in accordance with an embodiment of the invention.

FIG. 1 shows a schematic representation of an HF surgical device 1 including an adjusting means 3 which can be actuated manually in order to adjust the aforementioned different parameters. The HF surgical device 1 also includes a socket 9 having contact elements 4, 5, 6, 7 and 8. In the embodiment of FIG. 1, these contact elements are designed as sockets into which contact elements 4', 5', 6', 7', 8' (FIG. 2), embodied as plugs of a plug 10 (FIG. 2), can be inserted. Plug 10 acts as a first connecting means for connecting the connection cable 20 (FIG. 2) to the HF surgical device 1.

Figure 2:
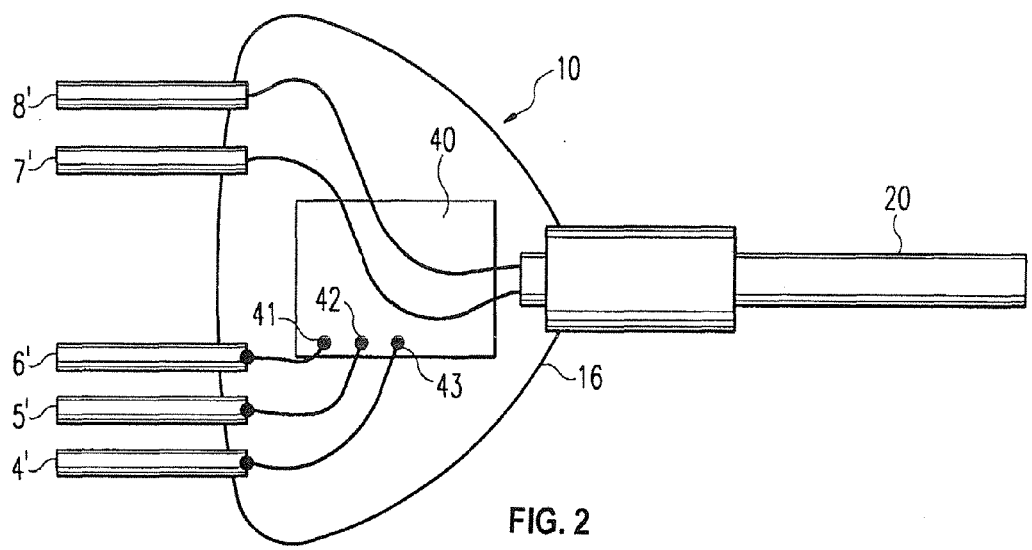
FIG. 2 is an illustration of a first connecting means, in accordance with an embodiment of the invention.

FIG. 2 shows programmable memory 40 which is disposed in the housing 16 of the plug 10. The programmable memory 40 includes programming connections 41, 42 and 43 which are connected to the contact elements 4', 5' and 6' of plug 10. These programming connections 41, 42 and 43 are simultaneously also signal outputs. The programming is performed via programming connections 41, 42 and 43 in a way known in the art (e.g., via elevated voltages).

Figure 3:
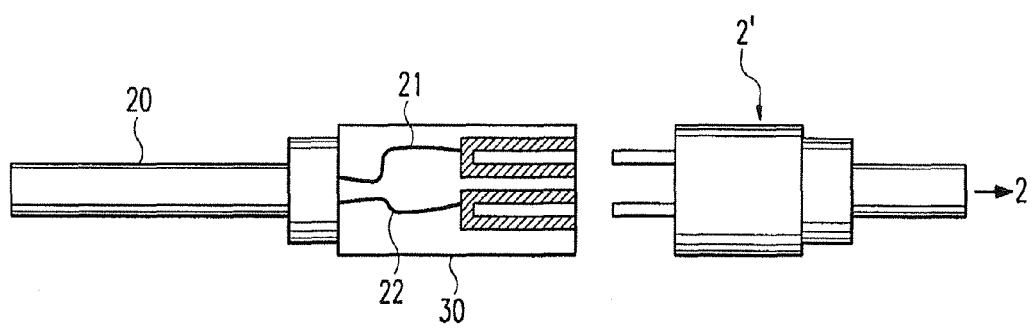
FIG. 3 is an illustration of second connecting means for connecting to an HF surgical instrument, in accordance with an embodiment of the invention.

As can be seen in FIG. 3, connected to the first connecting means 10 via a cable 20 is a second connecting means 30 which, in the exemplary embodiment, is a coupling for the insertion of plug 2' of an HF surgical instrument 2. The plug contacts of the plug 2' are connected via electrical lines 21 and 22 to the plug contacts 7' and 8' of the first connecting means 10. This allows high-frequency current to be supplied from the HF surgical device 1 via its contact elements 7 and 8 to the HF surgical instrument 2 via the plug contacts of 2'.

The programmable memory 40 is programmed such that, upon connection to the socket 9 and the corresponding supply of power, the coding of the contacts 4', 5' and 6' influences or presets the adjusting means 3 or the electrical appliances provided in the HF surgical device 1 in such a way that they are adapted to the particular HF surgical instrument 2 that is connected.

In a situation where one HF surgical instrument 2 is to be operated with a variety of HF surgical devices 1, the shape of the first connecting means 10 is adaptable to the different sockets 9 of the different HF surgical devices 1. In addition, the programmable memories 40 are appropriately adjusted to the "coding standards" required by the respective HF surgical devices 1. The programmable memories 40 are adjusted such that the HF surgical instrument 2 is operated in the same manner (e.g., with the same parameters) regardless of which of the different HF surgical devices 1 is used. Therefore, the invention facilitates alternating usability for any combination of instruments and devices.

In an additional embodiment of the invention, HF surgical instruments 2 having a specific plug 2' (e.g., HF surgical instruments permitting different maximum voltages) may themselves include coding devices, additional coding programs (sets of coding data) are stored in the programmable memory 40. Depending upon which HF surgical instrument 2 is connected to the second connecting means 30, the coding data sent to the HF surgical device 1 will change. The coding data set corresponding to the HF surgical instrument 2 is retrieved from the programmable memory 40 and sent to the HF surgical device 1 via the contact elements 4', 5' and 6' or 4, 5 and 6.

The programmable memory 40 of the disclosed embodiments may alternatively be disposed in the second connection means 30. The programmable memory 40 is preferably disposed in one of the first connecting means 10 or the second connecting means 30 so that a separate housing is not required.

It should be pointed out here that all the above described parts and in particular the details illustrated in the drawings are essential for the invention alone and in combination. Adaptations thereof are the common practice of persons skilled in the art.

The invention claimed is:

1. A connection cable comprising:
   a first connecting means designed for connection to a socket of a high-frequency surgical device;
   a second connecting means designed for connection to a high-frequency surgical instrument and connected via a cable to the first connecting means; and
   a programmable memory connected to contacts of the first connecting means,
   wherein the programmable memory controls an adjustment means of the high-frequency surgical device in accordance with a stored data set in order to adapt settings of the high-frequency surgical device to the high-frequency surgical instrument, and the programmable memory comprises programming connections that are connected to electrical contacts of the first connecting means, said programming connections allow for programming of the memory.

2. The connection cable according to claim 1, wherein the memory is disposed in the first connecting means.

3. The connection cable according to claim 1, wherein the programmable memory comprises programming connections that are connected to contacts of the second connecting means for programming the memory.

4. The connection cable according to claim 1, wherein the memory is disposed in the second connecting means.

5. The connection cable according to claim 1, wherein the adjustment means is disposed in the high-frequency surgical device and is connected to the programmable memory via the socket of the high-frequency surgical device.

6. A connection cable for connecting a high-frequency surgical instrument to a high-frequency surgical device, the connection cable comprising:
   a first plug for connection to the high-frequency surgical device;
   a second plug for connection to the high-frequency surgical instrument and connected via a cable to the first plug; and
   a memory disposed within a housing of the first plug,
   wherein the memory controls adjustment of the high-frequency surgical device in accordance with a stored data set corresponding to the high-frequency surgical instrument,
   wherein the memory is programmable and further comprises programming connections that are connected to electrical contacts of the first plug and wherein the programming connections allow for programming of the memory.

7. The connection cable of claim 6, wherein the a memory is connected to contacts of the first plug.

8. The connection cable of claim 6, wherein the memory contains a plurality of stored data sets corresponding to a plurality of types of high-frequency surgical devices.

9. The connection cable of claim 6, wherein the first plug is connected to a socket of the high-frequency surgical device.

10. The connection cable of claim 9, wherein the first plug is adaptable to fit the socket of a variety of high-frequency surgical instruments.

* * * * *